US010165997B2

(12) United States Patent
Baumgart et al.

(10) Patent No.: US 10,165,997 B2
(45) Date of Patent: Jan. 1, 2019

(54) SYSTEM FOR ACQUIRING A THREE-DIMENSIONAL IMAGE OF ARTERIES AND VEINS

(71) Applicant: Siemens Medical Solutions USA, Inc., Malvern, OH (US)

(72) Inventors: John Baumgart, Hoffman Estates, IL (US); Martin Trini, Schaumburg, IL (US); Michael J. Keller, Algonquin, IL (US)

(73) Assignee: Siemens Healthcare GmbH, Erlangen (DE)

( * ) Notice: Subject to any disclaimer, the term of this patent is extended or adjusted under 35 U.S.C. 154(b) by 97 days.

(21) Appl. No.: 15/201,792

(22) Filed: Jul. 5, 2016

(65) Prior Publication Data

US 2018/0012398 A1    Jan. 11, 2018

(51) Int. Cl.
*A61B 6/00* (2006.01)
*G06T 15/50* (2011.01)
(Continued)

(52) U.S. Cl.
CPC .............. *A61B 6/504* (2013.01); *A61B 6/466* (2013.01); *A61B 6/481* (2013.01); *G06T 5/50* (2013.01);
(Continued)

(58) Field of Classification Search
None
See application file for complete search history.

(56) References Cited

U.S. PATENT DOCUMENTS 6,246,897 B1 * 6/2001 Foo .................. G01R 33/56316
324/307
7,545,967 B1 * 6/2009 Prince ...................... G06T 5/50
128/920
(Continued)

OTHER PUBLICATIONS

Lei et al. "Separation of artery and vein in contrast-enhanced MRA images," Proc. SPIE Medical Imaging 2000, vol. 978, pp. 233-244.*
(Continued)

*Primary Examiner* — Soo Shin

(57) ABSTRACT

A system and method includes reception of first two-dimensional projection images of a patient volume, each of the first two-dimensional projection images having been acquired from substantially a respective one of a plurality of projection angles during presence of at least a portion of contrast medium in arteries within the patient volume, reception of second two-dimensional projection images of the patient volume, each of the second two-dimensional projection images having been acquired from substantially a respective one of the plurality of projection angles during presence of at least a portion of the contrast medium in veins within the patient volume, generation, for each of the plurality of projection angles, of a composite two-dimensional image based on one of the first two-dimensional projection images acquired from substantially the projection angle and one of the second two-dimensional projection images acquired from substantially the projection angle, generation of a three-dimensional image based on the generated composite two-dimensional images, and display of an image based on the three-dimensional image.

16 Claims, 7 Drawing Sheets

(51) Int. Cl.
  *G06T 19/00*   (2011.01)
  *G06T 5/50*    (2006.01)
  *G06T 7/00*    (2017.01)

(52) U.S. Cl.
  CPC .......... *G06T 7/0024* (2013.01); *G06T 15/503* (2013.01); *G06T 19/00* (2013.01); *G06T 2207/10116* (2013.01); *G06T 2207/20224* (2013.01); *G06T 2207/30101* (2013.01); *G06T 2210/41* (2013.01)

(56)          References Cited

U.S. PATENT DOCUMENTS

| | | | | |
|---|---|---|---|---|
| 2007/0232901 | A1* | 10/2007 | Benndorf | A61B 6/481 |
| | | | | 600/425 |
| 2008/0056438 | A1* | 3/2008 | Zellerhoff | A61B 6/4441 |
| | | | | 378/11 |
| 2011/0037761 | A1* | 2/2011 | Mistretta | A61B 6/4441 |
| | | | | 345/419 |
| 2011/0038517 | A1* | 2/2011 | Mistretta | A61B 6/02 |
| | | | | 382/128 |
| 2011/0299749 | A1* | 12/2011 | Rauch | G06T 7/254 |
| | | | | 382/130 |
| 2013/0188771 | A1* | 7/2013 | Kyriakou | A61B 6/032 |
| | | | | 378/19 |
| 2017/0100037 | A1* | 4/2017 | Harmelin | A61B 5/0035 |

OTHER PUBLICATIONS

Wu et al. "Clinical Experience of HYPR Flow," Proc. Intl. Soc. Mag. Reson. Med. 16 (2008).*

* cited by examiner

SYSTEM FOR ACQUIRING A THREE-DIMENSIONAL IMAGE OF ARTERIES AND VEINS

BACKGROUND

According to conventional angiographic x-ray imaging, contrast media are used to enhance the contrast of blood-carrying structures within patient anatomy. For example, a contrast medium is introduced into a patient volume (e.g., via intravenous injection) and an x-ray image of the volume is acquired while the medium is located within the volume. In the x-ray image, structures which contain the medium (e.g., veins and arteries) appear darker than they would otherwise appear.

Currently, if a physician desires to acquire three-dimensional x-ray data of both arteries and veins, two separate three-dimensional acquisitions are required, with each of the two three-dimensional acquisitions comprising a mask volume and a fill volume. Each mask volume and fill volume, in turn, requires acquisition of a series of two-dimensional x-ray images. Each of the two fill volume acquisitions exposes the patient to a separate contrast medium injection, and each acquired two-dimensional x-ray image exposes the patient to a dose of x-ray radiation. Moreover, the four acquired volumes are independent of one another and require significant processing to be displayed coherently.

Systems are desired which provide efficient acquisition and presentation of three-dimensional images of blood-carrying components.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated for carrying out the described embodiments. Various modifications, however, will remain readily apparent to those in the art.

Some embodiments facilitate the generation of a three-dimensional image of arteries and veins. According to some embodiments, projection images of an arterial fill volume are acquired soon after contrast medium injection, and projection images of a venous fill volume are acquired thereafter, without an additional contrast medium injection. The projection images are combined and the combined projection images are used to generate a three-dimensional image of arteries and veins.

Figure 1:
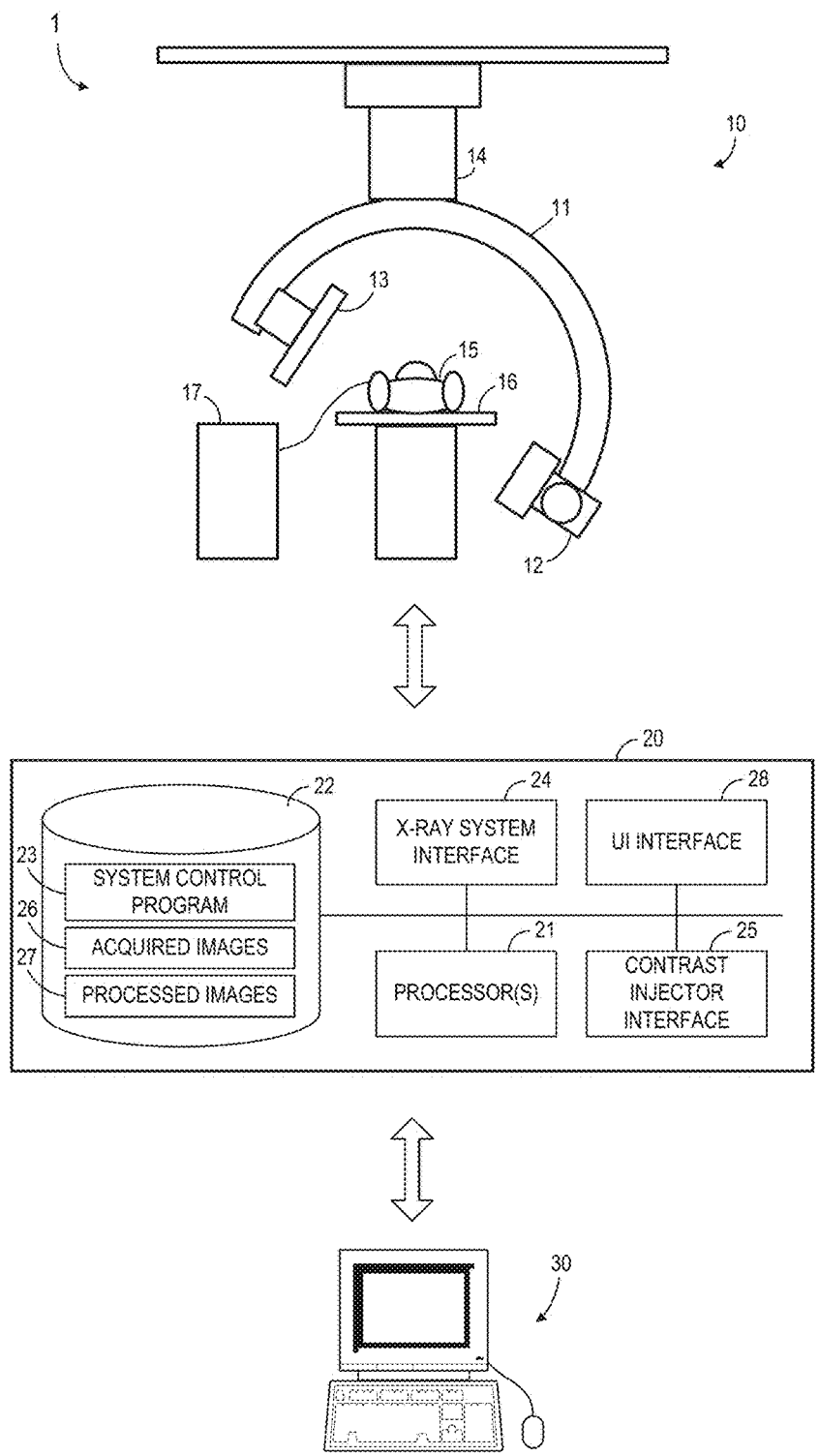
FIG. 1 illustrates a system according to some embodiments.

FIG. 1 illustrates system 1 according to some embodiments. System 1 includes x-ray imaging system 10, control and processing system 20, and operator terminal 30. Generally, and according to some embodiments, x-ray imaging system 10 introduces contrast medium into a patient volume and acquires x-ray images of the patient volume. Control and processing system 20 controls x-ray imaging system 10 and receives the acquired images therefrom. Control and processing system 20 processes the images as described below and provides the processed images to terminal 30 for display thereby. Such processing may be based on user input received by terminal 30 and provided to control and processing system 20 by terminal 30.

X-ray imaging system 10 comprises C-arm 11 on which radiation source 12 and radiation detector 13 are mounted. C-arm 11 is mounted on support 14 and is configured to translate clockwise or counter-clockwise with respect to support 14. This translation rotates radiation source 12 and radiation detector 13 around a central volume while maintaining the physical relationship therebetween. Embodiments are not limited to C-arm-based imaging systems.

Radiation source 12 may comprise any suitable radiation source, including but not limited to a Gigalix™ x-ray tube. In some embodiments, radiation source 12 emits electron, photon or other type of radiation having energies ranging from 50 to 150 keV.

Radiation detector 13 may comprise any system to acquire an image based on received x-ray radiation. In some embodiments, radiation detector 13 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In other embodiments, radiation detector 13 converts received photons to electrical charge without requiring a scintillator layer. The photons are absorbed directly by an array of amorphous selenium photoconductors. The photoconductors convert the photons directly to stored electrical charge. Radiation detector 13 may comprise a CCD or tube-based camera, including a light-proof housing within which are disposed a scintillator, a mirror, and a camera.

The charge developed and stored by radiation detector 13 represents radiation intensities at each location of a radiation field produced by x-rays emitted from radiation source 12. The radiation intensity at a particular location of the radiation field represents the attenuative properties of tissues lying along a divergent line between radiation source 12 and the particular location of the radiation field. The set of radiation intensities acquired by radiation detector 13 may therefore represent a two-dimensional projection image of these tissues.

Contrast injector 17 may comprise any known device or devices suitable to controllably introduce contrast medium into a patient volume. As described above, structures which contain contrast medium appear darker in x-ray images than they would otherwise appear. Contrast injector 17 may include a reservoir for each of one or more contrast media, and a patient interface such as medical-grade tubing terminating in a hollow needle.

System 20 may comprise any general-purpose or dedicated computing system. Accordingly, system 20 includes one or more processors 21 configured to execute processorexecutable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of system control program 23. One or more processors 21 may execute system control program 23 to move C-arm 14, to cause radiation source 12 to emit radiation, to control detector 13 to acquire an image, to cause injector 17 to introduce contrast medium into a volume of patient 15, and to perform any other function. In this regard, system 20 includes x-ray system interface 24 and contrast injector interface 25 for communication with system 10.

Images acquired from system 10 are stored in data storage device 22 as acquired images 26, in DICOM or another data format. Each acquired image 26 may be further associated with details of its acquisition, including but not limited to imaging plane position and angle, imaging position, radiation source-to-detector distance, patient anatomy imaged, patient position, contrast medium bolus injection profile, x-ray tube voltage, image resolution and radiation dosage.

Processor(s) 21 may execute system control program 23 to process acquired images 26, resulting in processed images 27. Processed images 27 may be provided to terminal 30 via UI interface 28 of system 20. UI interface 28 may also receive input from terminal 30, which is used to control processing of acquired images 26 as described below.

Terminal 30 may simply comprise a display device and an input device coupled to system 20. Terminal 30 displays acquired images 26 and/or processed images 27 received from system 20 and may receive user input for controlling display of the images, operation of imaging system 10, and/or the processing of acquired images 26. In some embodiments, terminal 30 is a separate computing device such as, but not limited to, a desktop computer, a laptop computer, a tablet computer, and a smartphone.

Each of system 10, system 20 and terminal 30 may include other elements which are necessary for the operation thereof, as well as additional elements for providing functions other than those described herein.

According to the illustrated embodiment, system 20 controls the elements of system 10. System 20 also processes images received from system 10. Moreover, system 20 receives input from terminal 30 and provides processed images to terminal 30. Embodiments are not limited to a single system performing each of these functions. For example, system 10 may be controlled by a dedicated control system, with the acquired images being provided to a separate image processing system over a computer network or via a physical storage medium (e.g., a DVD).

Figure 2:
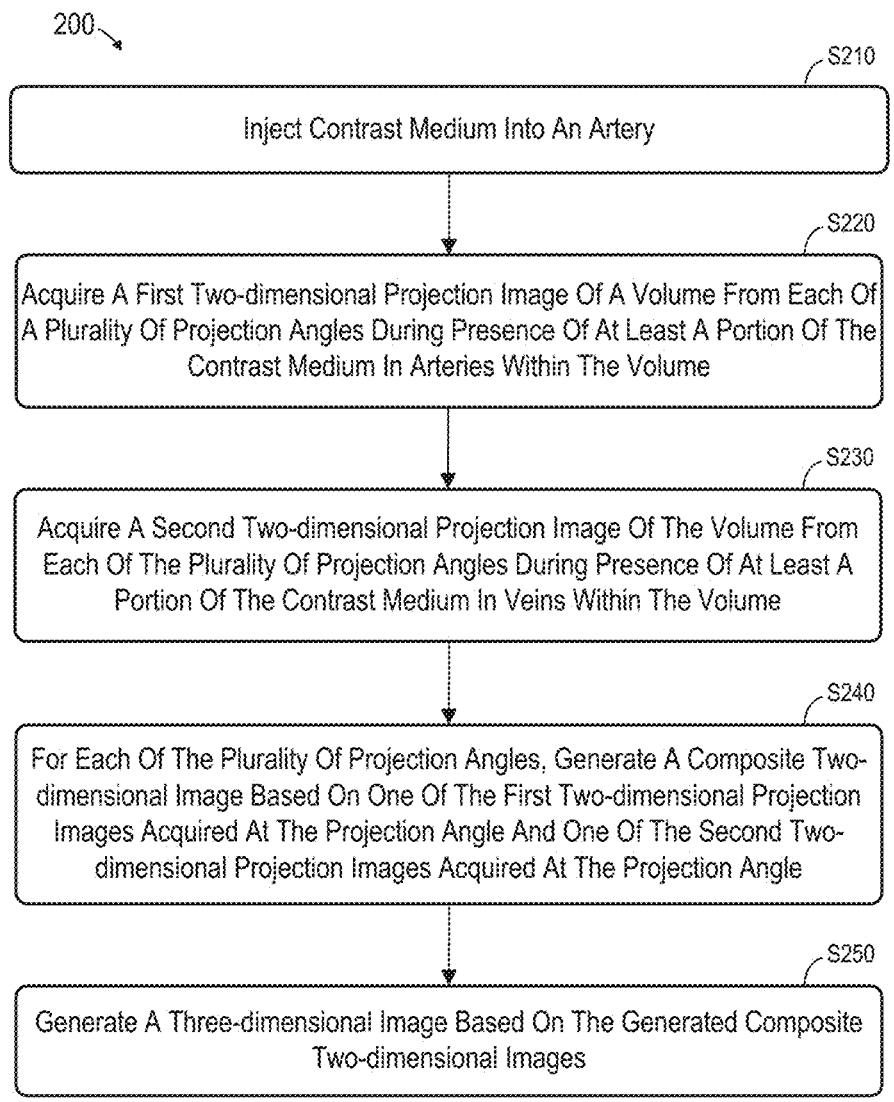
FIG. 2 is a flow diagram of a process according to some embodiments.

FIG. 2 is a flow diagram of process 200 according to some embodiments. Process 200 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape. Examples of these processes will be described below with respect to the elements of system 1, but embodiments are not limited thereto.

It will be assumed that, prior to S210, the patient is positioned for imaging according to known techniques. For example, and with reference to the elements of system 1, patient 15 is positioned on table 16 to place a particular volume of patient 15 between radiation source 12 and radiation detector 13. Table 16 may be adjusted to assist in positioning the patient volume as desired. As is known in the art, such positioning may be based on a location of a volume of interest, on positioning markers located on patient 15, on a previously-acquired planning image, and/or on a portal image acquired after an initial positioning of patient 15 on table 16.

Initially, at S210, contrast medium is injected into an artery. According to some embodiments of S210, system 20 instructs contrast injector 17 to introduce contrast medium into an artery of patient 15. The parameters of the medium introduction (e.g., flow rate, location, volume) may be controlled by system control program 23 as is known in the art.

Next, at S220, a first projection image of a volume including the artery is acquired from each of a plurality of projection angles. The first projection images are acquired during presence of at least a portion of the contrast medium in arteries within the volume. The projection angles are predetermined such that the acquired first projection images are suitable to reconstruct a three-dimensional image of the volume according to reconstruction techniques that are or become known.

According to some embodiments, system 20 instructs system 10 to move C-arm 11 so that radiation source 12 and radiation detector 13 will generate images of the patient volume at the predetermined projection angles after introduction of the contrast medium into the patient volume and while at least a portion of the contrast medium is present within arteries of the volume. Radiation source 12 is powered by a high-powered generator to emit x-ray radiation toward radiation detector 13 at the predetermined projection angles. The parameters of the x-ray radiation emission (e.g., timing, x-ray tube voltage, dosage) may be controlled by system control program 23 as is known in the art. Radiation detector 13 receives the emitted radiation and produces a set of data (i.e., a projection image) for each projection angle at S220. The projection images may be received by system 20 and stored among acquired images 26.

At S230, a second projection image of a volume including the artery is acquired from each of the plurality of projection angles. The second projection images are acquired during presence of at least a portion of the contrast medium in veins within the volume. The projection angles at which the second projection images are acquired are intended to be substantially similar to those at which the first projection images were acquired but system tolerances may prevent the projection angles from being precisely identical.

Accordingly, acquisition of the first projection images and of the second projection images at S220 and S230 is timed such that the first projection images are acquired while the contrast medium is present in the arteries of interest to an extent required to provide suitable contrast within an arterial fill volume generated based on the first projection images, and that the second projection images are acquired while the contrast medium is present in the veins of interest to an extent required to provide suitable contrast within a venous fill volume generated based on the second projection images.

Next, at S240, and for each of the projection angles, a composite two-dimensional image is generated based on one of the first two-dimensional projection images acquired at the projection angle and one of the second two-dimensional projection images acquired at the projection angle.

Figure 3:
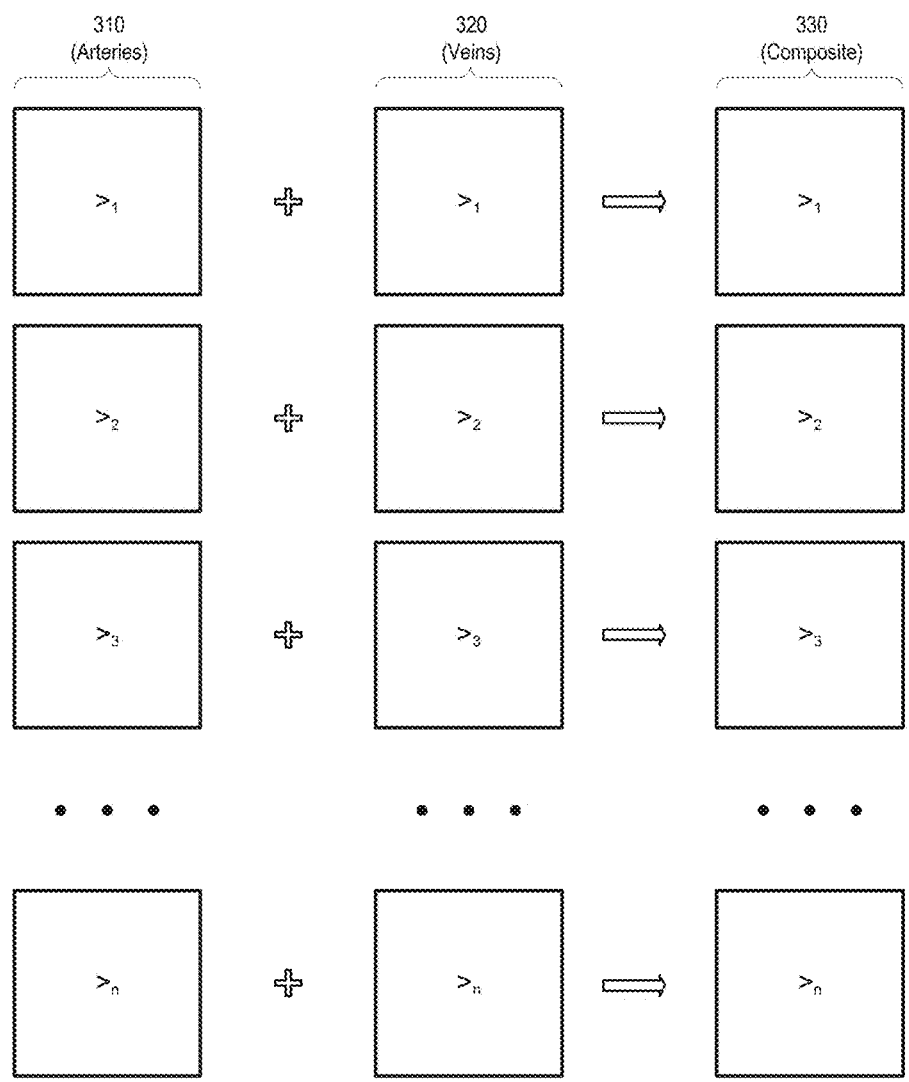
FIG. 3 illustrates combination of two-dimensional x-ray images according to some embodiments.

FIG. 3 illustrates S240 according to some embodiments. Projection images 310 represent the first projection images acquired at S220, and projection images 320 represent the second projection images acquired at S230. Each of projection images 310 and 320 is associated with a projection angle (e.g., $>_1, >_2, \ldots, >_n$) at which the image was acquired.

As shown, according to some embodiments of S240, each pair of projection images 310 and 320 which is associated with a given projection angle is used to create a composite two-dimensional image 330 which is also associated with the given projection angle. Accordingly, after execution of S240, one of composite projection images 330 is associated with each of the projection angles.

Generation of the composite two-dimensional images need not be purely additive as suggested in FIG. 3. Any algorithm for creating a third image based on a first image and a second image may be employed at S340. Further details of S240 according to some embodiments are provided below with respect to FIG. 7.

Figure 4:
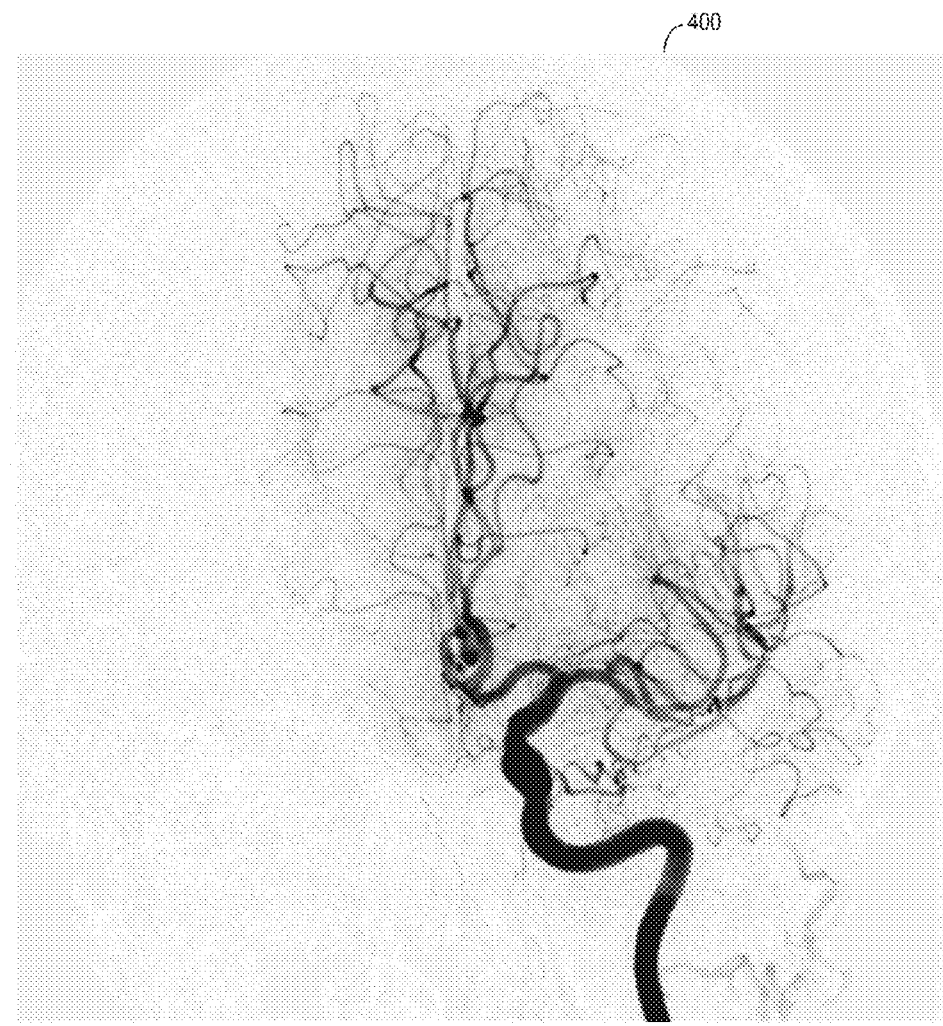
FIG. 4 illustrates a two-dimensional x-ray image according to some embodiments.
Figure 5:
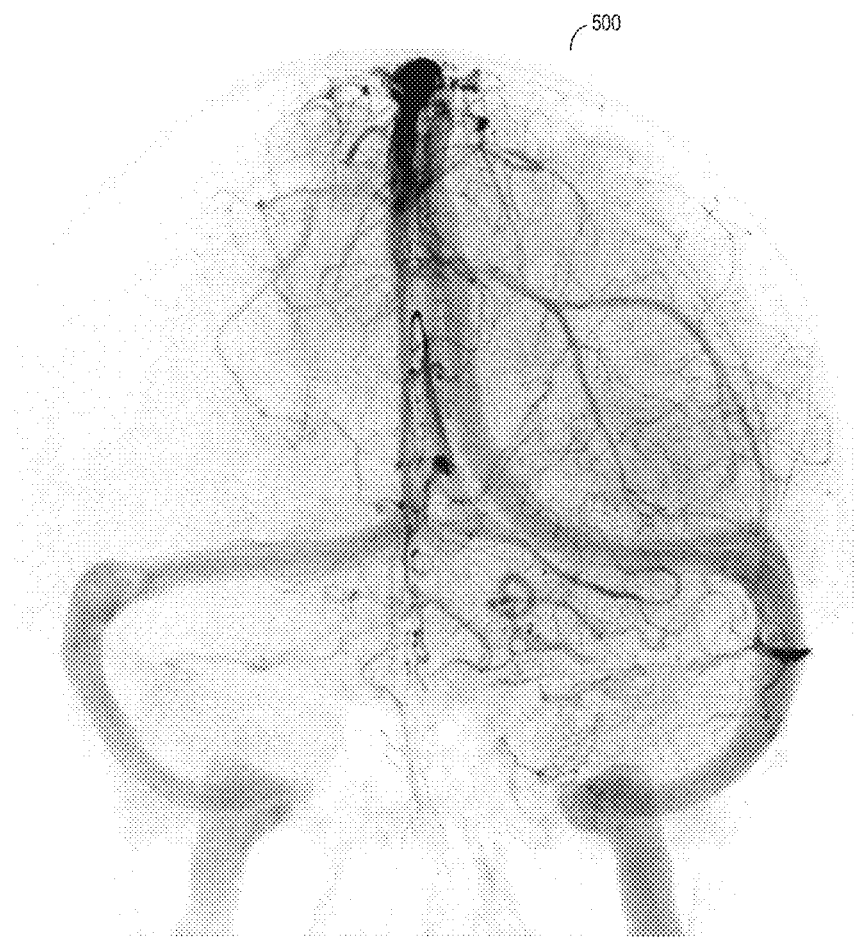
FIG. 5 illustrates a two-dimensional x-ray image according to some embodiments.

FIG. 4 is an example of first projection image 400 acquired at a particular projection angle at S220 according to some embodiments. First projection image 400 depicts arteries within a patient volume having enhanced contrast due to the presence of contrast medium therein. Similarly, FIG. 5 is an example of second projection image 500 acquired at the particular projection angle at S230 according to some embodiments. Second projection image 500 depicts veins within the patient volume having enhanced contrast due to the presence of contrast medium therein.

Figure 6:
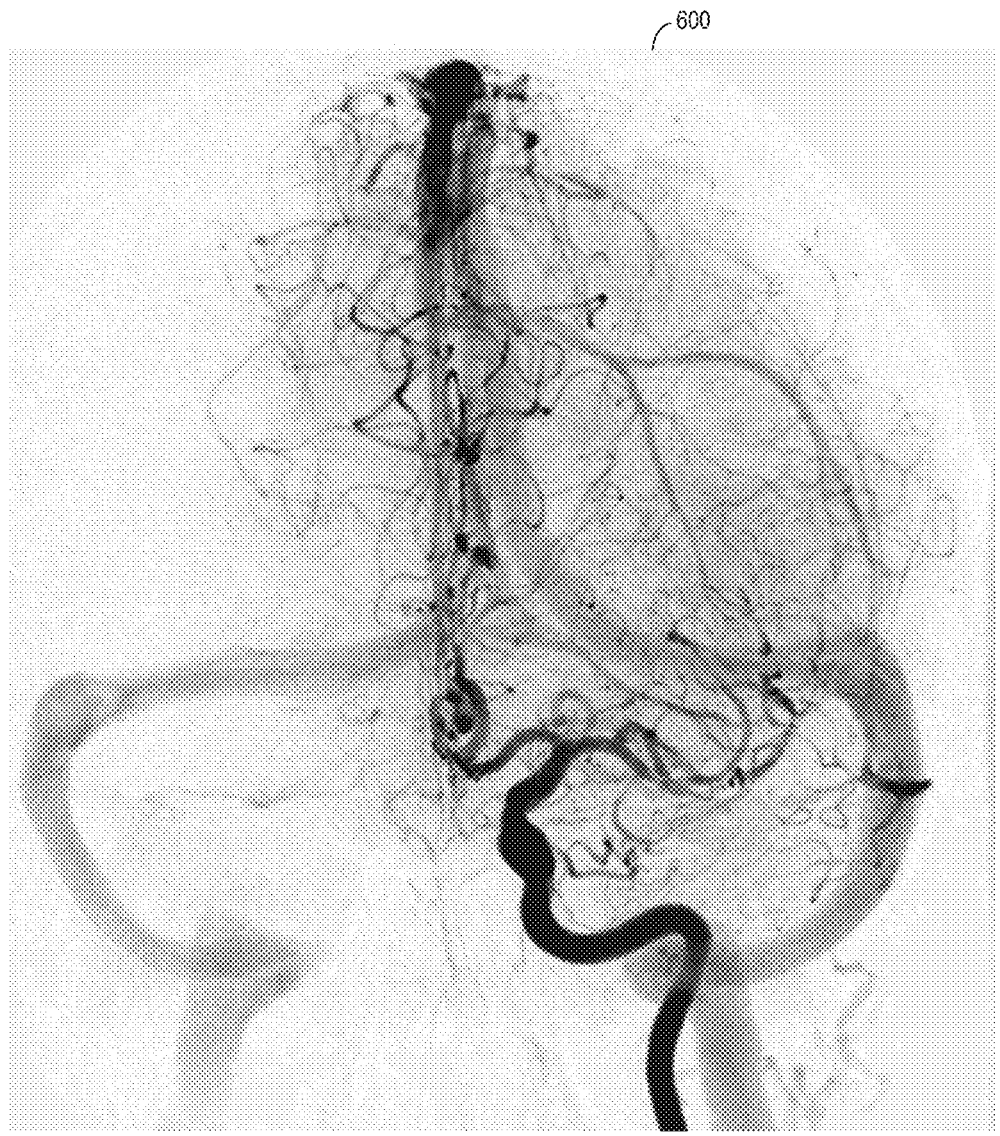
FIG. 6 illustrates a combined two-dimensional x-ray image according to some embodiments.

Composite image 600 of FIG. 6 was generated based on images 400 and 500 according to some embodiments. Composite image 600 is associated with the same projection angle from which images 400 and 500 were acquired. Composite image 600 shows both veins and arteries including contrast medium. According to some embodiments, composite image 600 consists of, for each pixel therein, the maximum value of the pixel values of arterial image 400 and venous image 500 (i.e., $C_{x,y}=\text{Max }[A_{x,y},V_{x,y}]$).

A three-dimensional image is generated based on the composite two-dimensional images at S250. The three-dimensional image may be generated using any three-dimensional reconstruction techniques that are or become known. The three-dimensional composite image may present both arteries and veins as enhanced by contrast medium.

The composite images and the three-dimensional image may be stored among processed images 27. An image based on the three-dimensional image may be displayed by terminal 30. The displayed image may be the three-dimensional image itself or a two-dimensional slice of the three-dimensional image.

Accordingly, some embodiments efficiently provide a three-dimensional arterial and venous image while reducing patient exposure to radiation and contrast medium with respect to conventional systems.

According to some embodiments, a two-dimensional mask image is acquired at each projection angle before introduction of the contrast medium into the artery at S210. Since the mask image is acquired without the presence of the contrast medium, the mask image depicts background anatomic detail of the patient volume. The mask image acquired at a given projection angle may be registered with and subtracted from the first projection image and the second projection image acquired at the given projection angle, prior to combination thereof at S240. The resulting first projection image and the second projection image, and the three-dimensional image which is eventually generated at S250 based thereon, thereby portray only the vessel components of the patient volume which include contrast medium.

According to some embodiments, a first mask image is acquired at each projection angle before introduction of the contrast medium into the artery at S210, and the first projection images of contrast-enhanced arteries are acquired at S220. The contrast medium is given time to flush out and a second mask image is then acquired at each projection angle. Contrast medium is again introduced and the second projection images of contrast-enhanced veins are acquired at S230. The first and second mask images are registered with and subtracted from their respective first projection images and second projection images and flow then continues as described above.

Figure 7:
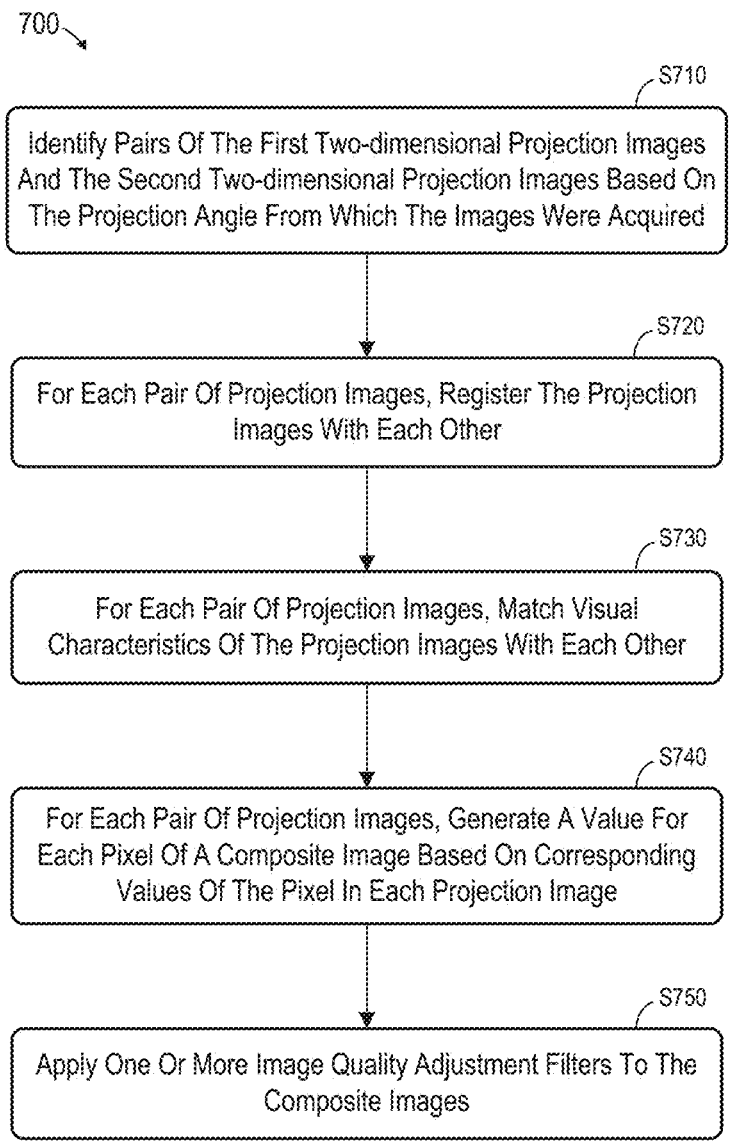
FIG. 7 is a flow diagram of a process according to some embodiments.

Process 700 of FIG. 7 is an example of S240 according to some embodiments. S240 is not limited to the steps of process 700 or to the order of the steps.

Initially, at S710, pairs of images are identified. A pair of images consists of one of the first two-dimensional projection images and one of the second two-dimensional projection images. As described above and illustrated in FIG. 3, each image of a pair of images was acquired at a (substantially) same projection angle.

The images of each pair of images are registered with one another at S720. Registration is intended to remove motion artifacts between the images of a pair, by correcting for any relative motion of the patient between acquisitions of the images of the pair. Any motion correction technique may be employed at S720.

For each pair of images, visual characteristics of the images are matched at S730. Such matching may include modifying one image of a pair to match a brightness, contrast, signal strength and/or other visual characteristic of the other image of the pair. S730 may comprise histogram matching in some embodiments.

Next, for each pair of images, a value is generated at S740 for each pixel of a composite image based on corresponding values of the same pixel in each image of the pair. Mathematically, $C_{x,y}=f(A_{x,y},V_{x,y})$. The generated value may simply be equal to the maximum value of the pixel in the two images as described above. In some embodiments, the value is a weighted sum such as $C_{x,y}=wA_{x,y}+(1-w)V_{x,y}$.

According to some embodiments, known processing to the composite images at S750 in order to enhance edges, adjust brightness, collimate the field of view, and/or to conform the images to the display properties of the display device of terminal 30. Processing at S750 may include one or more of denoising filters, median filters and low-pass filters.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
an interface coupled to a processor configured to:
receive a plurality of first two-dimensional projection images of a patient volume, each of the first two-dimensional projection images having been acquired at one of a plurality of first respective projection angles during presence of, and following an injection of, at least a portion of a first contrast medium in arteries within the patient volume; and
receive a plurality of respective second two-dimensional projection images of the patient volume, each of the second two-dimensional projection images having been acquired at one of a plurality of second respective projection angles during presence of, and with no additional injection of, at least a portion of the first contrast medium in veins within the patient volume, each of the plurality of second respective projection angles within system tolerances of being identical to a respective one of the plurality of first projection angles;

the processor configured to:

for each of the plurality of first respective projection angles, generate a composite two-dimensional image based on one of the first two-dimensional projection images acquired at one of the plurality of first respective projection angles and one of the second two-dimensional projection images acquired at one of the plurality of second respective projection angles that is within system tolerances of being identical to the one of the plurality of first respective projection angles;

the processor configured to generate the composite two-dimensional image by generating a weighted sum value for each pixel of the composite two-dimensional image based on corresponding values of the pixel in the identified respective one of the first two-dimensional projection images and the identified respective one of the second two-dimensional projection images;

generate a three-dimensional image based on the generated composite two-dimensional images; and a display configured to display at least one of the three-dimensional image and a two-dimensional slice of the three-dimensional image.

2. The system according to claim 1, further comprising: an X-ray detector and an X-ray source operable to acquire the first two-dimensional projection images and the second two-dimensional projection images.

3. The system according to claim 2, further comprising a contrast injector to inject the contrast medium into the patient volume.

4. The system according to claim 1, including:

the interface configured to receive two-dimensional mask images of the patient volume, each of the two-dimensional mask images having been acquired at a projection angle within system tolerances of being identical to a respective one of the plurality of first respective projection angles prior to presence of the first contrast medium in arteries within the patient volume; and the processor configured to generate the composite two-dimensional images by, for each projection angle, subtracting a respective one of the two-dimensional mask images from a respective one of the first two-dimensional projection images and from a respective one of the second two-dimensional projection images.

5. The system according to claim 1, generation of the composite two-dimensional images including, for each first respective projection angle, registering the respective one of the first two-dimensional projection images with the respective one of the second two-dimensional projection images.

6. The system according to claim 5, including:

the interface configured to receive two-dimensional mask images of the patient volume, each of the two-dimensional mask images having been acquired at a projection angle within system tolerances of being identical to a respective one of the plurality of first respective projection angles prior to presence of the first contrast medium in arteries within the patient volume; and the processor configured to generate the composite two-dimensional images by for each projection angle, subtracting a respective one of the two-dimensional mask images from a respective one of the first two-dimensional projection images and from a respective one of the second two-dimensional projection images.

7. The system according to claim 6, generation of the composite two-dimensional images including:

for each first respective projection angle, identifying the respective one of the first two-dimensional projection images acquired at the first respective projection angle and identifying the respective one of the second two-dimensional projection images.

8. The system according to claim 5, generation of the composite two-dimensional images including:

for each first respective projection angle, identifying the respective one of the first two-dimensional projection images acquired at the first respective projection angle and identifying the respective one of the second two-dimensional projection images.

9. A method comprising:

receiving a plurality of first two-dimensional projection images of a patient volume, each of the first two-dimensional projection images having been acquired at one of a plurality of first respective projection angles during presence of, and following an injection of, at least a portion of a first contrast medium in arteries within the patient volume;

receive a plurality of respective second two-dimensional projection images of the patient volume, each of the second two-dimensional projection images having been acquired at one of a plurality of second respective projection angles during presence of, and with no additional injection of, at least a portion of the first contrast medium in veins within the patient volume, each of the plurality of second respective projection angles within system tolerances of being identical to a respective one of the plurality of first projection angles;

generating, for each of the plurality of first respective projection angles, a composite two-dimensional image based on one of the first two-dimensional projection images acquired at one of the plurality of first respective projection angles and one of the second two-dimensional projection images acquired at one of the plurality of second respective projection angles that is within system tolerances of being identical to the one of the plurality of first respective projection angles;

generating the composite two-dimensional image including generating a weighted sum value for each pixel of the composite two-dimensional image based on corresponding values of the pixel in the identified respective one of the first two-dimensional projection images and the identified respective one of the second two-dimensional projection images;

generating a three-dimensional image based on the generated composite two-dimensional images; and displaying at least one of the three-dimensional image and a two-dimensional slice of the three-dimensional image.

10. The method according to claim 9, further comprising:

acquiring the first two-dimensional projection images; and acquiring the second two-dimensional projection images.

11. The method according to claim 10, further comprising injecting the contrast medium into the patient volume.

12. The method according to claim 9, further comprising:

receiving two-dimensional mask images of the patient volume, each of the two-dimensional mask images having been acquired at a projection angle within system tolerances of being identical to a respective one of the plurality of first respective projection angles prior to presence of the first contrast medium in arteries within the patient volume; and generating the composite two-dimensional images by, for each projection angle, subtracting a respective one of the two-dimensional mask images from a respective one of the first two-dimensional projection images and from a respective one of the second two-dimensional projection images.

13. The method according to claim 9, generating the composite two-dimensional images including, for each first respective projection angle, registering the respective one of the first two-dimensional projection images with the respective one of the second two-dimensional projection images.

14. The method according to claim 13, further comprising receiving two-dimensional mask images of the patient volume, each of the two-dimensional mask images having been acquired at a projection angle within system tolerances of being identical to a respective one of the plurality of first respective projection angles prior to presence of the first contrast medium in arteries within the patient volume; and generating the composite two-dimensional images by, for each projection angle, subtracting a respective one of the two-dimensional mask images from a respective one of the first two-dimensional projection images and from a respective one of the second two-dimensional projection images.

15. The method according to claim 14, generating the composite two-dimensional images including:
for each first respective projection angle, identifying the respective one of the first two-dimensional projection images acquired at the first respective projection angle and identifying the respective one of the second two-dimensional projection images.

16. The method according to claim 13, generating the composite two-dimensional images including:
for each first respective projection angle, identifying the respective one of the first two-dimensional projection images acquired at the first respective projection angle and identifying the respective one of the second two-dimensional projection images.

* * * * *